United States Patent [19]

Palfreyman et al.

[11] Patent Number: 5,198,433
[45] Date of Patent: Mar. 30, 1993

[54] LACTAMIMIDES AS CALCIUM ANTAGONISTS

[75] Inventors: Michael G. Palfreyman; Norbert L. Wiech; Hsien C. Cheng; John M. Kane, all of Cincinnati, Ohio

[73] Assignee: Merrell Dow Pharmaceuticals Inc., Cincinnati, Ohio

[21] Appl. No.: 918,350

[22] Filed: Jul. 21, 1992

Related U.S. Application Data

[62] Division of Ser. No. 850,183, Mar. 11, 1992, Pat. No. 5,158,945, which is a division of Ser. No. 763,799, Sep. 23, 1991, Pat. No. 5,128,337, which is a division of Ser. No. 620,226, Nov. 29, 1990, Pat. No. 5,082,837, which is a division of Ser. No. 212,544, Jun. 28, 1988, Pat. No. 5,010,072.

[51] Int. Cl.$^5$ .................. A61K 31/33; A61K 31/40; A61K 31/44; A61K 31/55
[52] U.S. Cl. .................. 514/212; 514/183; 514/319; 514/352; 514/426
[58] Field of Search ............... 514/212, 183, 319, 352, 514/426

[56] References Cited

U.S. PATENT DOCUMENTS

| | | | |
|---|---|---|---|
| 3,378,438 | 4/1968 | Gatzo et al. | 514/212 |
| 3,783,162 | 1/1974 | Grisar et al. | 514/329 |
| 3,803,170 | 4/1974 | Grisar et al. | 260/326.85 |
| 3,816,457 | 6/1974 | Grisar et al. | 260/329 AM |
| 3,833,559 | 9/1974 | Grisar et al. | 260/239 B |
| 3,838,851 | 9/1974 | Grisar et al. | 260/239 B |
| 3,840,523 | 10/1974 | Grisar et al. | 260/239 B |
| 3,840,524 | 10/1974 | Grisar et al. | 260/239 B |
| 3,845,071 | 10/1974 | Grisar et al. | 260/309.6 |
| 3,852,269 | 12/1974 | Grisar et al. | 260/239 B |
| 3,873,520 | 3/1975 | Blohm et al. | 260/239 B |
| 3,881,006 | 4/1975 | Grisar et al. | 514/212 |
| 3,890,445 | 6/1975 | Grisar et al. | 514/212 |
| 3,894,002 | 7/1975 | MacKenzie et al. | 260/239 B |
| 3,900,565 | 8/1975 | Grisar et al. | 514/426 |
| 4,055,561 | 10/1977 | Grisar et al. | 260/239 B |

OTHER PUBLICATIONS

Grupp et al, *Br. J. Pharmacol.* 70:429–442, (1980).
Rampe et al, *J. Pharmacol. Exp. Ther.* 243:402–407, (1987).
Lee et al, *J. Pharmacol. Exp. Ther.* 233:611–616, (1985).

*Primary Examiner*—Allen J. Robinson
*Attorney, Agent, or Firm*—Michael J. Sayles

[57] ABSTRACT

Applicants have discovered that certain previously known lactamimide derivatives possess, as a class, valuable calcium channel blocking activity. By virtue of this calcium antagonism activity the compounds are antihypertensives and will have other activities associated with calcium antagonists.

6 Claims, 4 Drawing Sheets

-LOG [DRUG], (M)

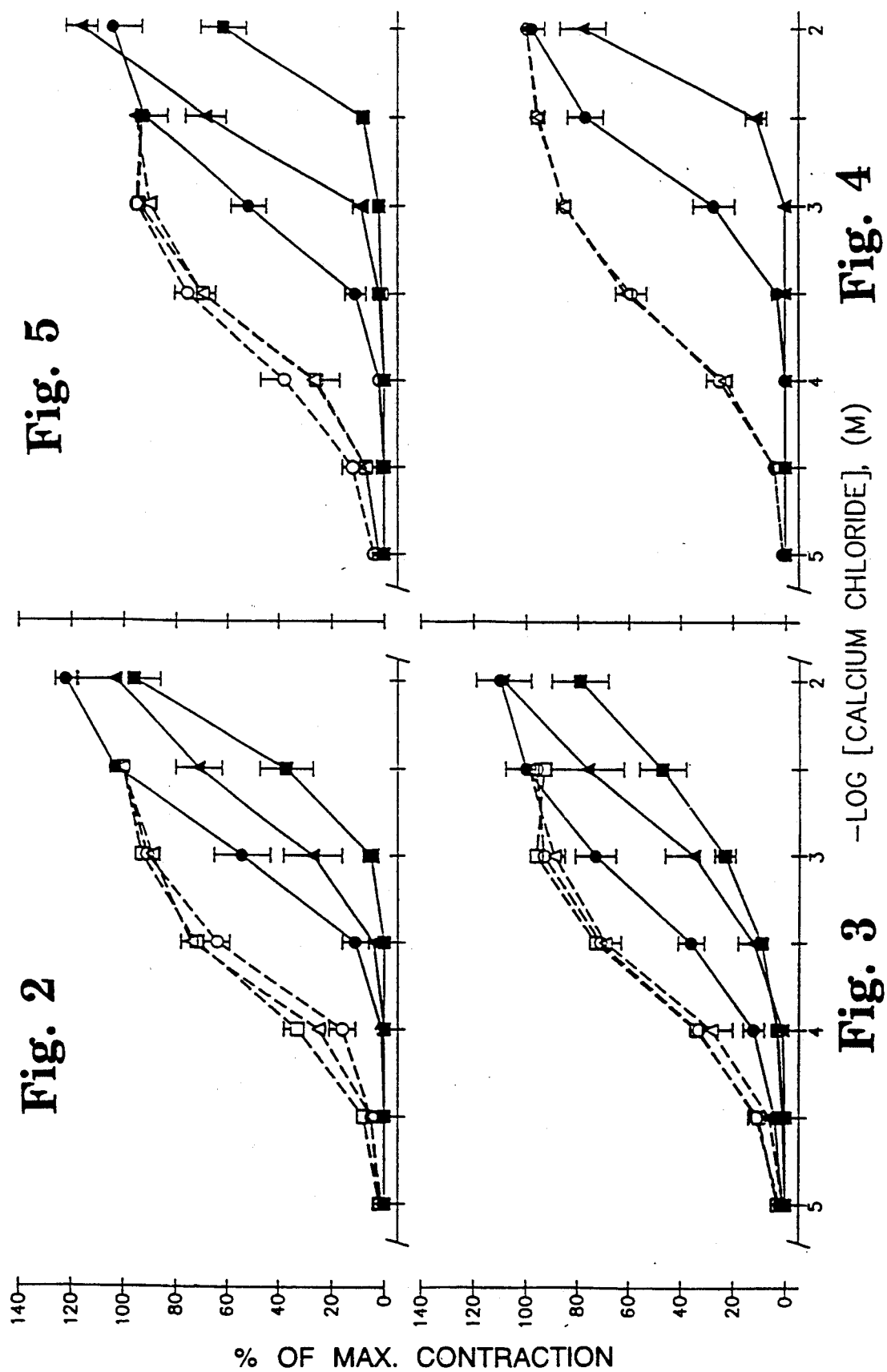

LACTAMIMIDES AS CALCIUM ANTAGONISTS

This is a division of application Ser. No. 07/850,183, filed Mar. 11, 1992, U.S. Pat. No. 5,158,945, which is a division of application Ser. No. 763,799, filed Sep. 23, 1991, now U.S. Pat. No. 5,128,337, which is a division of application Ser. No. 620,226, filed Nov. 29, 1990, now U.S. Pat. No. 5,082,837, which is a division of application Ser. No. 07/212,544, filed Jun. 28, 1988, now U.S. Pat. No. 5,010,072.

This invention relates to the use of certain lactamimides as calcium antagonists and their pharmaceutical uses as antiangina, vasodilating, antihypertensive, antimanic, and anticonvulsant agents and for protection against ischemic injury and for conditions where an excess of intracellular calcium is known to be detrimental to the organism.

BACKGROUND OF THE INVENTION

The compounds described herein are known. The compounds employed in this method have been described in the following patents: U.S. Pat. No. 3,894,002, issued Jul. 8, 1975; U.S. Pat. No. 3,852,269, issued Dec. 3, 1974; Belgian Pat. No. 783,276 granted Apr. 30, 1973; U.S. Pat. No. 3,873,520 issued Mar. 25, 1975; U.S. Pat. No. 3,803,170 issued Apr. 9, 1974; U.S. Pat. No. 3,838,151 issued Sep. 24, 1974; U.S. Pat. No. 3,833,559 issued Sep. 3, 1974; U.S. Pat. No. 3,783,162 issued Jan. 1, 1974; U.S. Pat. No. 3,900,565 issued Sep. 19, 1975; U.S. Pat. No. 3,881,006 issued Apr. 29, 1975; Belgian Pat. No. 814,114 granted May 15, 1974; U.S. Pat. No. 3,840,524 issued Oct. 8, 1974; U.S. Pat. No. 3,816,457 issued Jun. 11, 1974; U.S. Pat. No. 3,890,445 issued Jun. 17, 1975; U.S. Pat. No. 3,845,071 issued Oct. 29, 1974; U.S. Pat. No. 3,840,523 issued Oct. 8, 1974; Great Britain Pat. No. 1,201,848 issued Nov. 4, 1970; U.S. Pat. No. 3,378,438 issued Apr. 16, 1968.

It has been shown that calcium antagonists of diverse chemical structure interact in an allosteric manner with the calcium ion-channel protein. The chemical classes are exemplified by verapamil (a phenylalkylamine derivative), diltiazem (a benzothiazepine derivative) and the dihydropyridines, for example, nitrendipine. In binding experiments using [$^3$H]nitrendipine as the ligand, it has been shown that diltiazem enhances binding whereas verapamil displaces [$^3$H]nitrendipine in a noncompetitive manner.

The compound N-(cis-2-phenylcyclopentyl)azacyclotridecan-2-imine.HCl, a lactamimide has been reported to inhibit stimulated adenylate cyclase activity in a number of tissues. In addition, the compound has negative inotropic and chronotropic effects on isolated guinea pig hearts and these effects are reversed by the administration of calcium. Recently it was reported that this compound enhanced [3H]nitrendipine binding in rat cerebral cortical and cardiac homogenates in a similar manner to diltiazem and selectively reduced calcium currents with a potency similar to diltiazem.

We have now discovered that analogs of the above lactamimides belong to a novel chemical class displaying diltiazem-like calcium antagonism and are useful in the treatment of a wide variety of medical conditions.

SUMMARY OF THE INVENTION

Calcium channel blocking can be accomplished by the administration of a compound of the following general formula, or a pharmaceutically acceptable salt thereof or the individual geometric or optical isomers where applicable:

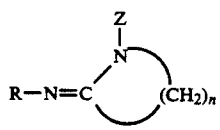

Formula I wherein
Z is hydrogen or lower alkyl of from 1 to 4 carbon atoms;
n is an integer of from 3 to 16;
R is
A) a straight or branched alkyl group of from 8 to 15 carbon atoms; or a lower alkoxyalkyl group wherein the alkyl moiety has from 8 to 15 carbon atoms and the alkoxy moiety has from 1 to 4 carbon atoms;
B) the group phenylalkyl wherein the alkyl moiety has from 1 to 6 carbon atoms and wherein the phenyl moiety is unsubstituted or substituted in which case the substituents may be attached at the ortho, meta or para-position of the phenyl ring and are chlorine, fluorine, bromine, lower alkyl having from 1 to 4 carbon atoms, lower alkoxy having from 1 to 4 carbon atoms, hydroxy or methylenedioxy;
C) the group

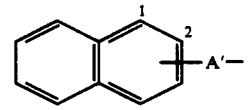

wherein A' is a straight or branched alkylene group of from 1 to 6 carbon atoms or benzyl and is attached to either the 1- or 2-position of the naphthalene ring, which is either unsubstituted or is mono- or di-substituted with a chlorine, fluorine, bromine, trifluoromethyl, a straight or branched alkyl group of from 1 to 12 carbon atoms, an alkoxy group of from 1 to 3 carbon atoms or $NO_2$;
D) the group 1- or 2-adamantyl or 1- or 2-norbornyl;
E) the group ortho, meta or para-biphenylyl;
F) the group 9-fluorenyl which is unsubstituted or substituted in which case the substituents may be attached to any one of the four available carbon atoms of each aromatic ring and are chlorine, bromine, fluorine, a lower alkyl group having from 1 to 4 carbon atoms, a lower alkoxy group having from 1 to 4 carbon atoms or $NO_2$;
G) dibenzocycloheptenyl;
H) the group

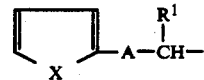

wherein X is oxygen or sulfur, A is a bond or an alkylene chain of from 1 to 3 carbon atoms, and $R^1$ is hydrogen, a straight or branched lower alkyl group having from 1 to 4 carbon atoms, a straight or branched lower alkenyl group having from 3 to 6 carbon atoms, cycloalkyl of from 3 to 6 carbon atoms or phenyl;

I) the group

wherein R2 is phenyl or a cycloalkyl group having from 3 to 6 carbon atoms, and $R^3$ is hydrogen or methyl;

J) the group

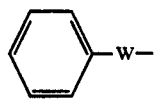

wherein W is a straight or branched alkylene chain having from 2 to 6 carbon atoms which is substituted with one phenyl group on any of the 6 carbon atoms with the proviso that the carbon atom adjacent to the exocyclic nitrogen atom must have at least one hydrogen attached to it;

K) the group

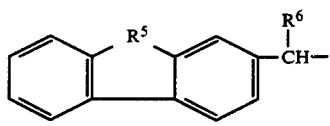

wherein R5 is oxygen, sulfur, —CH$_2$—, —CH$_2$CH$_2$— or —CH=CH—, and $R^6$ is hydrogen or a lower alkyl group of from 1 to 4 carbon atoms;

L) the group

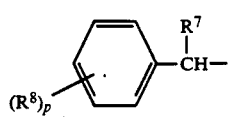

wherein $R^7$ is cycloalkyl of from 3 to 5 carbon atoms, R8 is hydrogen, lower alkoxy of from 1 to 4 carbon atoms or lower alkyl of from 1 to 4 carbon atoms, and p is the integer 1 or 2;

M) the group

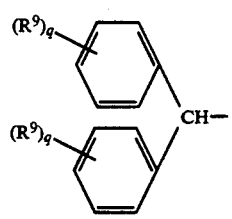

wherein $R^9$ is hydrogen, a straight or branched lower alkyl group of from 1 to 4 carbon atoms, chlorine, fluorine, bromine, CF$_3$, SCF$_3$, OCF$_3$, phenyl, phenoxy or a lower alkoxy group of from 1 to 4 carbon atoms and q is an integer of from 1 to 3;

N) the group

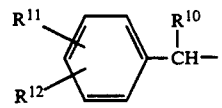

wherein $R^{10}$ is a lower alkyl group of from 1 to 4 carbon atoms, $R^{11}$ is hydrogen or lower alkyl of from 1 to 4 Carbon atoms, $R^{12}$ is an alkyl group having from 8 to 14 carbon atoms, an alkoxy group having from 8 to 14 carbon atoms, a cycloalkyl group having from 5 to 14 carbon atoms, phenyl, phenoxy, phenylalkyl wherein the alkyl moiety has from 1 to 4 carbon atoms, phenylalkoxy wherein the alkoxy moiety has from 2 to 4 carbon atoms, 2,2-diphenylvinyl or fluoren-9-ylidene;

O) the group

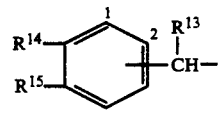

wherein the phenyl moiety is attached to the

moiety through the 1- or 2-position of the phenyl ring, $R^{13}$ is a lower alkyl group of from 1 to 4 carbon atoms and $R^4$ and $R^{15}$ taken together are (—CH$_2$—)$_3$, —CH$_2$CH$_2$C(CH$_3$)$_2$—, —(CH$_2$)$_4$— or —C(CH$_3$)$_2$CH$_2$CH$_2$C(CH$_3$)$_2$—;

with the proviso that when R is the group

Z is hydrogen;
and pharmaceutically acceptable acid addition salts thereof.

DETAILED DESCRIPTION OF INVENTION

It is apparent from the foregoing general Formula I that all of the compounds utilized in the instantly claimed invention contain a lactamimide ring having the structure

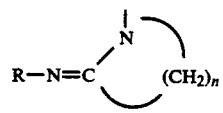

wherein n is an integer of from 3 to 16. Thus, the heterocyclic ring of the lactamimide moiety can be, for example, pyrrolidine, piperidine, hexahydroazepine, octahydroazocine, octahydroazonine, azacyclodecane, azacycloundecane, azacyclododecane or azacyclotridecane each of which is attached to the exocyclic nitrogen of the lactamimide moiety through the 2-position.

The term "dibenzocycloheptenyl" as used herein means both 5H-dibenzo[a,d]cycloheptenyl and 5e-,uns/H/ -dibenzo[a,c]-cycloheptenyl wherein the open valency is on any of the saturated carbon atoms of the cycloheptane ring. That is, the term dibenzocycloheptenyl means 5H-dibenzo[a,d]cyclohepten-5-yl,
5H-dibenzo[a,d]cyclohepten-10(or 11)-yl,
5H-dibenzo[a,c]cyclohepten-5(or 7)-yl, and
5H-dibenzo[a,c]cyclohepten-6-yl.

It is readily apparent that many of the "R" groups of the compounds of formula 1 have geometric or optical isomers. Unless specifically indicated, the individual isomers and their mixtures are intended.

For convenience and uniformity the compounds described herein are represented and named as substituted 2-iminoperhydroazacarbocyclics, as represented by general Formula I. It is known that compounds of this type as acid addition salts may also be represented by the tautomeric form illustrated by the following general Formula II:

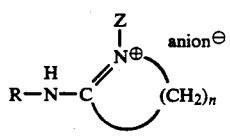

Formula II

This tautomerism has been discussed by R. Kwok and P. Pranc, *J. Org. Chem.* 32, 740 (1967). Structures of this formula could be named differently. In solution under the conditions of the therapeutic utility the proportions of each tautomeric form or the delocalization of the charge between the two nitrogen atoms will be dependent upon numerous factors including the nature of the substituents and the pH of the medium. This equilibrium state is conveniently illustrated by the following general Formula III:

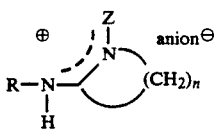

Formula III

The compounds of general Formula I wherein R is other than the group

as acid addition salts can exist in either tautomeric form, and it is understood that this invention relates to the use of compounds represented or named in either tautomeric form. In the above general Formulas II and III, the various symbols R, Z and n have the meanings defined in general Formula I. Further, when Z has the meaning hydrogen, other generally known tautomerism can occur.

Compounds of general Formula I wherein R represents

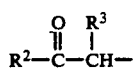

and Z represents hydrogen may exist as a cyclic tautomer of the following general Formula IV.

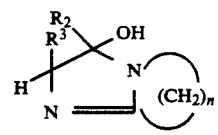

Formula IV

In the above general Formula IV the various symbols n, $R_2$, and $R_3$ have the meanings defined in general Formula I. It is understood that this invention embraces the use of the compounds of general Formula I wherein R is the group

when in the form as represented by general Formula IV. For purposes of convenience the compounds of this type are named herein as the cyclic form.

The compounds of the invention possess pharmacological activity and therefore they can be used as medicines. With the term "use" all industrial applicable aspect and acts of said use, including their embodiment into pharmaceutical compositions are intended. In particular, the compounds of the invention show in vitro calcium-antagonist activity and in vivo antihypertensive action. The compounds are thus useful as antianginals, vasodilators, antihypertensives, antimanics, anticonvulsants, and antiischemics and for those conditions in which an excess of intracellular calcium ion is involved, the so-called $Ca^{2+}$ overload hypothesis.

The ability of the compounds listed in Table 1 to act as calcium antagonists has been demonstrated in the following tests.

[$^3$H]d-cis-Diltiazem binding assays

The whole brain from male Sprague-Dawley rats (200-300 g) was dissected and homogenized in cold 50 mM Tris-HCl buffer (pH 7.4) for 2 x 30 second periods by Polytron (Brinkmann, setting No. 5). The homogenate was washed 2 times (48,000 ×g for 10 minutes, 4° C.) with intermittent resuspension of the pellet in fresh buffer. The final pellet was resuspended to an original tissue concentration of 100 mg/ml in Tris-HCl buffer. The binding assay of [$^3$H]d-cis-diltiazem was performed as previously described by J. L. Balwierczak and A. Schwartz, *Eur. J. Pharmacol.* 116:193-194, (1985) and H. Schoemaker and S. Z. Langer, *Eur. J. Pharmacol.* 111:273-277, (1985). Briefly, a 100 μl aliquot of the homogenate was incubated with 2.5 nM [$^3$H]d-cis-diltiazem in a total volume of 1 ml in 50 mM Tris-HCl buffer (pH 7.4) for 60 minutes at 25° C. or at 37° C. The reaction was terminated by rapid filtration under a vacuum through 0.05% polyethylenimine-pretreated Whatman GF/B glass fiber filters. Filters were immediately washed 2 times with 4 ml of cold Tris-HCl buffer. Pretreatment of the filters with 0.05% polyethylenimine served to eliminate [$^3$H]d-cis-diltiazem binding to the filter. The filters were dried and the radioactivity in the filters was extracted overnight in scintillation fluid. Samples were counted by liquid scintillation spectrophotometry with an efficiency of 43%. Specific [$^3$H]d-cis-diltiazem binding was defined as the difference in binding determined in the absence and presence of 30 μM d-cis-diltiazem and it represented 50-55% of the total amount of filter-retained radioactivity. Compounds were examined at concentrations from $10^{-8}$ to $10^{-3}$ M for their ability to inhibit [$^3$H]-diltiazem binding to membranes. pKi values were determined by the method of Cheng and Presoff, *Biochem Pharmacol.* 22: 3099–3108 (1973).

[$^3$H]Nitrendipine binding assay

Membranes were prepared from the hearts of male Sprague-Dawley rats and [$^3$H]nitrendipine binding was conducted as described in detail by H. R. Lee, et al., *J. Pharmacol Exp. Ther.* 233:611–616, (1985), as modified by F. J. Ehlert, et al., *Biochem. Biophys. Rec. Common.* 104:937–943, (1982). The ability of compounds tested at $10^{-6}$ and $10^{-7}$ M to enhance [$^3$H]nitredepine binding was taken as indicative of diltiazem-like calcium antagonistic properties.

K$^\pm$-depolarized taenia and small intestine

Strips of taenia from the caecum or pieces of ileum, 2 cm in length, from male guinea pigs (200–400 g) were set up in isolated organ baths in Ca$^{++}$-free K$^+$ Tyrode's solution (mM NaCl 137, KCl 40, NaH$_2$PO$_4$ 0.4, NaHCO$_3$ 11.9, glucose 5.5) and gassed with 95% O$_2$, 5% CO$_2$ at 37° C. Contractions were measured with isotonic transducers with a 1 g load. Cumulative dose-response curves were obtained. Tissues were then washed and incubated with the compounds for 20–25 minutes and then Ca$^{++}$ concentration response curves re-established. The preparations were shown to be stable for at least 5 hours and to give reproducible dose-response curves to Ca$^{++}$. Dose ratios were determined graphically at ED$_{50}$ values from the Ca$^{++}$ dose-response curve and Schild plots were constructed to determine pA$_2$ value using inverse regression line analysis. Alternatively, when only one concentration of an antagonist was used, pA2 values were calculated according to the method of J. M. Van Rossum, *Arch. Int. Pharmacodyn Ther.* 143: 299–330 (1963).

The results of these tests are summarized in Tables 2 and 3 and in FIGS. 1–4.

TABLE 1

Calcium Antagonist and [$^3$H]Diltiazem Displacing Properties of Lactamimides

| Test Compound Number (as HCl unless otherwise indicated) | n | R | pA$_2$* | pKi** |
|---|---|---|---|---|
| 1 | 11 | 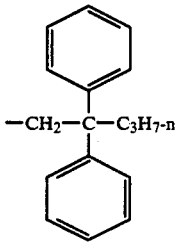 | 7.27 | 6.49 |
| 2 | 11 | 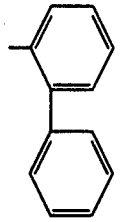 | 6.59 | 6.51 |
| 3 | 11 | 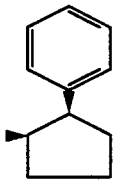 | 6.66 | 6.41 |
| 4 | 11 | 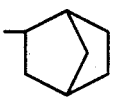 | 6.07 | 5.92 |

TABLE 1-continued
Calcium Antagonist and [$^3$H]Diltiazem
Displacing Properties of Lactamimides
Test Compound Number
(as HCl unless otherwise indicated)
| # | n | R | pA$_2$* | pKi** |
|---|---|---|---------|-------|
| 5V | 6 | 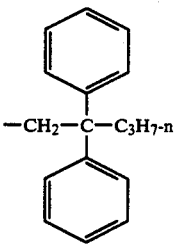 —CH$_2$—C—C$_3$H$_7$-n (with two phenyl groups) | 6.60 | N.T. |
| 6 | 5 | 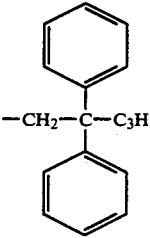 —CH$_2$—C—C$_3$H$_7$-n (with two phenyl groups) | 6.64 | N.T. |
| 7 | 4 | 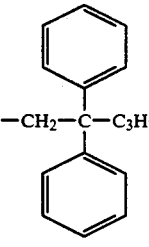 —CH$_2$—C—C$_3$H$_7$-n (with two phenyl groups) | 6.15 | N.T. |
| 8 | 6 | 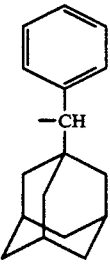 —CH- adamantyl with phenyl | 6.63 | 6.72 |
| 9 | 5 | 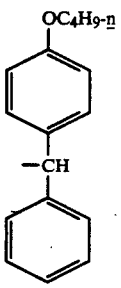 —CH with phenyl and p-OC$_4$H$_9$-n phenyl | 5.86 | 6.17 |

TABLE 1-continued
Calcium Antagonist and [³H]Diltiazem
Displacing Properties of Lactamimides
| Test Compound Number (as HCl unless otherwise indicated) | n | R | pA₂* | pKi** |
|---|---|---|---|---|
| 10 | 5 | 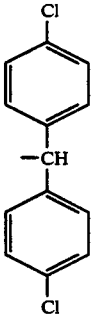 | 6.33 | 6.08 |
| 11 | 5 | 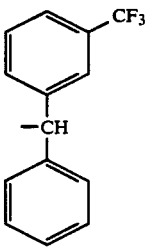 | 5.60 | 5.92 |
| 12 | 5 | 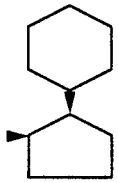 | 5.54 | 5.54 |
| 13 | 5 |  | 5.47 | 4.70 |
| 14 | 7 | 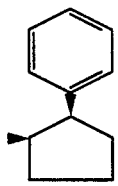 | 4.84 | 5.26 |
| 15 | 5 | 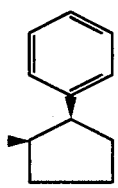 | N.T. | 4.16 |
| 16 | 3 | 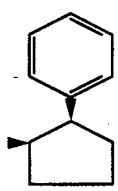 | N.T. | 4.96 |

TABLE 1-continued

Calcium Antagonist and [³H]Diltiazem
Displacing Properties of Lactamimides

Test Compound
Number
(as HCl unless otherwise indicated)

| # | n | R | pA₂* | pKi** |
|---|---|---|------|-------|
| 17 | d-cis | (diltiazem-like structure with OCH₃, S, N-CH₂CH₂-N(CH₃)₂, O-C(=O)-CH₃, .HCl) | 7.38 | 7.42 |
| 18 | l-cis | (same structure as 17) | N.T. | 5.39 |
| 19 | 3 | CH₂-(phenyl with OCH₃ and OH) | N.T. | N.T. |
| 20 | 5 | —CH₂CH₂CH(C₆H₅)₂ | 6.19 | N.T |
| 21 | 5 | —CH₂—CH(Ph)(Ph) | 6.14 | — |
| 22 | 5 | —CH₂—C(Ph)(Ph)(C₃H₇-n) | 6.31 | — |
| 23 | 4 | (piperidin-2-ylidene)NH—CH₂—C(Ph)(Ph)(n-C₃H₇) .HCl | 6.04 | — |
| 24 | 6 | (azocan-2-ylidene)NH—CH₂—C(Ph)(Ph)(n-C₃H₇) | 6.63 | — |
| 25 | 5 | (+)— CH(CH₃)-naphthyl (or tautomer) | 5.47 | — |

TABLE 1-continued

Calcium Antagonist and [$^3$H]Diltiazem
Displacing Properties of Lactamimides

| Test Compound Number (as HCl unless otherwise indicated) | n | R | pA$_2$* | pKi** |
|---|---|---|---|---|
| 26 | 5 | 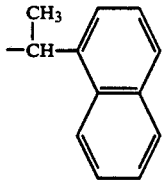<br>(or tautomer) | 5.18 | — |

V = Fumarate
N.T.—Not Tested
*pA2 values calculated by the method of O. Arunlakshana & H. O. Schild, Br. J. Pharmacol. Chemother. 14:45–58 (1959) using guinea pig ileum or taenia preparations.
**pKi values calculated by the method of Y. C. Cheng & W. H. Prusoff, Biochem. Pharmacol. 22:3099–3108, (1973) using diplacement of 3H diltiazem to rat brain membranes at 25° C. n = 3

In Table 1, the chemical nomenclature for each of the test compounds is as follows:

Test Compound 1: N-(2,2-diphenylpentyl)azacyclotridecan-2-imine;
Test Compound 2: 2-(o-biphenylylimino)azacyclotridecane;
Test Compound 3: 2-[(cis-2-phenylcyclopentyl)imino]azacyclotridecane;
Test Compound 4: 2-(2-norbornylimino)azacyclotridecane:
Test Compound 5: 2-[(2,2-diphenylpentyl)imino]octahydroazocine;
Test Compound 6: hexahydro-2-[(2,2-diphenylpentyl)imino]azepine;
Test Compound 7: 2-[(2,2-diphenylpentyl)imino]piperidine;
Test Compound 8: 2-[[α-(1-adamantanyl)benzyl]imino]octahydroazocine;
Test Compound 9: 2-[(p-butoxy-α-phenylbenzyl)imino]hexahydroazepine;
Test Compound 10: 2-[(p-chloro-α-[p-chlorophenyl]benzyl)imino]hexahydroazepine;
Test Compound 11: hexahydro-N-[phenyl[3-(trifluoromethyl)phenyl]methyl]-2H-azepin-2-imine;
Test Compound 12: 2-[(cis-2-cyclohexylcyclopentyl)imino]hexahydroazepine;
Test Compound 13: 2-(2-adamantanylimino)hexahydroazepine;
Test Compound 14: octahydro-2-[(cis-2-phenylcyclopentyl)imino]azonine;
Test Compound 15: hexahydro-2-[(cis-2-phenylcyclopentyl)imino]azepine;
Test Compound 16: 2-[(cis-2-phenylcyclopent-1-yl)imino[pyrrolidine;
Test Compound 17: (1)-cis-5-2-(dimethylamino)etnyl]2,3 -dihydro-3-hydroxy-2-(p-methoxyphenyl)-1,5-benzothiazepin-4(5H)-one acetate;
Test Compound 18: (1)-cis-5-[2-(dimethylamino)ethyl]2,3-dihydro-3-hydroxy-2-(p-methoxyphenyl)-1,5-benzothiazepin-4(5H)-one acetate;
Test Compound 19: 2-methoxy-4-[[[3-[(4-methylphenyl)methylene]-2-pyrrolidinyliden]amino]methyl]phenol;
Test Compound 20: hexahydro-2-[3,3-diphenylpropylimino)azepine;
Test Compound 21: hexahydro-2-(2,2-diphenylethylimino)azepine;
Test Compound 22: hexahydro-2-[(2,2-diphenylpentyl)imino]azepine;
Test Compound 23: 2-[(2,2-diphenylpentyl)imino]piperidine;
Test Compound 24: 2-[(2,2-diphenylpentyl)imino]octahydroazocine;
Test Compound 25: (+)-hexahydro-N-[1-(1-naphthalenyl)ethyl]2H-azepin-2-imine; and
Test compound 26: (-)-hexahydro-N-[1-(1-naphthalenyl)ethyl]2H-azepin-2-imine.

TABLE 2

Temperature dependence of displacement of
[$^3$H]d-cis-diltiazem by d-cis-diltiazem and lactamides

| Compound | 25° C. | 37° C. |
|---|---|---|
| d-cis-Diltiazem | 43 ± 7 | 110 ± 25 |
| 3 | 280 ± 30 | 403 ± 77 |
| 19 | 1260 ± 90 | 1900 ± 230 |

IC$_{50}$ values were calculated from dose-response curves at concentrations giving 50% inhibition of the specific [3H]d-cis-diltiazem binding to rat whole brain membranes. Ligand concentration was 2.5 nM, n = 3.

TABLE 3

Enhancement of [$^3$H]nitrendipine binding to rat heart membranes by d-cis-diltiazem and lactamimides

| | 25° C. | | 37° C. | |
|---|---|---|---|---|
| Compound | 10$^{-7}$M | 10$^{-6}$M | 10$^{-7}$M | 10$^{-6}$M |
| 1 | 119 ± 6 | 123 ± 6 | 252 ± 13 | 224 ± 14 |
| 2 | 117 ± 7 | 123 ± 10 | 152 ± 9 | 152 ± 15 |
| 3 | 102 ± 1 | 112 ± 2 | 141 ± 8 | 165 ± 13 |
| 5 | — | — | 111 ± 9 | 122 ± 3 |
| 4 | 105 ± 4 | 106 ± 4 | 108 ± 7 | 116 ± 8 |
| d-cis-Diltiazem | 96 ± 5 | 83 ± 8 | 218 ± 4 | 262 ± 10 |

Values are the mean ± SEM of single experiments run in triplicate at the concentrations of drugs indicated. Ligand concentration was 0.1 nM and control specific binding was 49.6 ± 1.7 fmol/mg protein.

The compounds may be administered in various manners to achieve the desired effect. The compounds may be administered alone or in the form of pharmaceutical preparations to the patient being treated either orally or parenterally, such as, intravenously or intramuscularly. The formulation of suitable pharmaceutical compositions can be carried out by one skilled in the art according to the general common knowledge in the art, and referring to reference books, such as Remington's Pharmaceutical Sciences Handbook, Mack Publishing Company, U.S.A. The amount of compound administered will vary with the severity of the condition to be treated, and the mode of administration. For oral administration the calcium antagonist effective amount of compound is from about 0.01 mg/kg (milligrams per kilogram) of patients body weight per day to about 10 mg/kg of patient body weight per day and preferably from about 0.05 mg/kg of patient body weight per day to about 5 mg/kg of patient body weight per day.

For parenteral administration the calcium antagonist effective amount of compound is from about 0.001 mg/kg of patient body weight per day up to about 5 mg/kg of patient body weight per day and preferably from about 0.01 mg/kg of patient body weight per day up to about 2 mg/kg of patient body weight per day.

For oral administration a unit dosage may contain, for example, from 0.50 to 100 mg of the active ingredient. For parenteral administration a unit dosage may contain, for example, from 0.05 to 70 mg of the active ingredient. Since the compounds of the invention generally possess a long lasting duration of action they might be conveniently administered once or twice a day, however, repetitive daily administrations may be, at least in some instances, desirable and will vary with the conditions of the patient and the mode of administration. As used herein, the term "patient" is taken to mean a warm blooded animal, humans included.

For oral administration the compounds can be formulated into solid or liquid preparations such as capsules, pills, tablets, troches, powders, solutions, suspensions or emulsions. The solid unit dosage form can be a capsule which can be of the ordinary gelatin type, either hard or soft, containing, for example, lubricants and inert fillers, such as lactose, sucrose and cornstarch. In another embodiment the compounds of the invention can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of mineral petroleum, animal, vegetable or synthetic origin. For example, peanut oil, soybean oil and mineral oil. In general, water, saline, aqueous dextrose and related sugar solutions, ethanol and glycols such as propylene glycol or polyethylene glycol can be used as liquid carriers for injectable solutions.

For rectal administration the compounds are administered in the form of suppositories, admixed with conventional vehicles such as, for example, cocoa butter, wax, spermaceti, polyvinylpyrrolidone, or polyoxyethylenglycols and their derivatives.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation. The oral route is generally the preferred route of administration of the compounds of the invention, while the capsule is generally the preferred pharmaceutical formulation.

An illustrative composition for tablets is the following:

|     |                                   | mg/tablet |
|-----|-----------------------------------|-----------|
| (a) | 2-(2-norbornylimino)azacyclo tridecane | 15        |
| (b) | Lactose                           | 33        |
| (c) | Corn starch                       | 11.25     |
| (d) | Sucrose 3% starch                 | 12.75     |
| (e) | Corn starch paste (10%)           | 1.50      |
| (f) | Zinc stearate                     | 1.50      |

A preferred embodient of this invention is the use of the compounds described herein wherein n is an integer of from 0 to 16, and within this preferred embodiment the use of the compounds wherein n is the integer 11 is more preferred. Also preferred are those compounds of formula 1 wherein R is selected from the groups D, E, and L. More preferred are those compounds of formula 1 wherein R is selected from 1- or 2-norbornyl, especially 2-norbornyl, ortho-biphenyl, or a diphenylalkyl group of from 2 to 6 carbon atoms wherein the phenyl groups are substituted on the $\beta$ or $\delta$ carbon atom of the alkyl chain, especially a 2,2-diphenylpentyl or 3,3-diphenylpropyl group. Especially preferred are those compounds of formula 1 wherein n is 11 and wherein R is 2-norbornyul, orthobiphenyl or a 2,2-diphenylpentyl group.

Illustrative examples of compounds of this invention are
2-(8-methoxyoctylimino)azacyclotridecane,
2-(12-n-propoxydodecylimino)azacyclododecane,
hexyhydro-2-(10-butoxydecylimino)azepine,
2-(11-ethoxyundecylimino)piperidine,
2-(12-n-propoxydodecylimino)pyrrolidine,
2-(benzylimino)pyrrolidine,
2-(p-chlorobenzylimino)piperidine,
hexahydro-2(3',4'-methylenedioxybenzylimino)azepine,
2-(p-tolylimino)azacyclodecane,
octahydro-2-(p-anisylimino)azonine,
octahydro-2-(p-n-butoxyphenethylimino)azocine,
hexahydro-2-(o-propylphenethylimino)azepine,
hexahydro-2-(o-tolylimino)azepine,
hexahydro-2-(benzylimino)azepine,
hexahydro-2-[1-(6-dodecyl-1-naphthyl)ethylimino]azepine,
2-(7-trifluoromethyl-2-naphthylmethylimino)octahydroazonine,
hexahydro-2-(1-naphthylmethylimino)azepine,
2-[1-naphthyl)ethylimino]piperidine,
2-(6-bromo-2-methoxy-1-naphthylmethylimino)azacyclotridecane,
2-[1-(5,8-dimethyl-1-naphthyl)ethylimino]hexahydroazepine,
2-[1-(1-naphthyl)ethylimino]octahydroazopine,
hexahydro-2-α-(1-naphthyl)benzylimino]azepine,
2-1(adamantylimino)azacyclotridecane,
2-(2-adamantyl)hexahydroazepine,
2-(1-adamantylimino)azacycloundecane,
1-methyl-2-(2-adamantylimino)azacyclododecane,
2-(2-adamantylimino)azacyclodecane,
2-(2-norbornylimino)azacyclododecane,
1-methyl-2-(1-norbornylimino)azacyclodecane,
2-(2-norbornylimino)piperidine,
1-ethyl-2-(2-norbornylimino)hexahydroazepine,
2-(2-norbornylimino)pyrrolidine, 2-(1-norbornylimino)azacyclotridecane,
2-(o-biphenylylimino)azacyclotridecane,
2-(m-biphenylylimino)hexahydroazepine,
1-methyl-2-(p-biphenylylimino)piperidine,
2-(o-biphenylylimino)pyrrolidine,
2-(9-fluorenylimino)azacyclotridecane,
2-(9-fluorenylimino)pyrrolidine,
2-(2-nitro-9-fluorenylimino)piperidine,
2-(3-methoxy-9-fluorenylimino)hexahydroazepine,
2-(9-fluorenylimino)octahydroazepine,
2-(3,6-dimethyl-9-fluorenylimino)hexahydroazepine,
1-methyl-2-(9-fluorenylimino)azacyclotridecane,
2-(3-methyl-7-chloro-9-fluorenylimino)azacyclododecane,
2-(9-fluorenylimino)azacycloundecane,
2-(4-bromo-9-fluorenylimino)azacyclodecane,
2-(3-n-propoxy-9-fluorenylimino)pyrrolidine,
2-(2-fluoro-9-fluorenylimino)piperidine,
2-[(10,11-dihydro-5H-dibenzo[a,d]cycloheptan-5-yl)imino]hexahydroazepine,
2-[(10,11-dihydro-5H-dibenzo[a,d]cycloheptan-5-yl)imino]octahydroazocine,
2-[(10,11-dihydro-5H-dibenzo[a,d]cycloheptan-5-yl)imino]octahydroazonine,
2-[(10,11-dihydro-5H-dibenzo[a,d]cycloheptan-5-yl)imino]azacyclotridecane,
2-[(10,11-dihydro-5H-dibenzo[a,d]cycloheptan-5-yl)imino]azacyclododecane,
2-[(10,11-dihydro-5H-dibenzo[a,d]cycloheptan-5-yl)imino]piperidine,
2-[(10,11-dihydro-5H-dibenzo[a,d]cycloheptan-5-yl)imino]pyrrolidine,
2-[(1-benzylcyclopentyl)imino]pyrrolidine,
2-[[α-(2-thienyl)benzyl]imino]azacyclotridecane,
2-[(2-thienyl)imino]hexahydroazepine,
1-methyl-2-(2-thienylimino)hexahydroazepine,
hexahydro-2-[1-(2-thienyl)propylimino]azepine,
2-(furfurylimino)hexahydroazepine,
2-[[α-(2-furyl)benzyl]imino]octahydroazocine,
1-ethyl-2-[[o-(2-furyl)benzyl]imino]octahydroazocine,
2-[[α-(2-thienyl)benzyl]imino]hexahydroazapine,
2-[1-(2-thienyl)propylimino]pyrrolidine,
2-[(α-cyclopropyl-2-thienyl)imino]hexahydroazepine,
2-[β-(2-thienyl)isopropylimino]hexahydroazepine,
2-[2-(1-[2-furyl]pent-4-enyl)imino]azacyclotridecane,
2-[2-(1-[2-furyl]pent-4-enyl)imino]azacyclododecane,
2-[(α-cyclopentyl-2-thienyl)imino]piperidine,
2-[(α-[2-furyl]benzyl)imino]hexahydroazapine,
2-[3-[4-(2-furyl)-4-cyclopentyl]butylimino)azepine,
2-(-[1-(2-furyl)hex-4-enyl]imino)azacyclotridecane,
2,3,5,6,7,8-hexahydro-2-methyl-2-phenylimidazo[1,2-a]pyridin-3-ol,
2,3,6,7-tetrahydro-2-methyl-3-phenyl-5H-pyrolo[1,2-a]imidazol-3-ol,
2,3,6,7-tetrahydro-2,2-dimethyl-3-phenyl-5H-pyrrolo[1,2-a]imidazo-3-ol,
2,3,5,6,7,8,9,10-octahydro-2-methyl-3-phenylimidazo[1,2-a]azocine-3-ol,
2,3,5,6,7,8-hexahydro-3-phenylimidazo[1,2-a]pyridin-3-ol,
3-cyclohexyl-2,3,6,7,8,9-hexahydro-2-methyl-5H-imidazo[1,2-a]azopine-3-ol,
hexahydro-2-[(8-methyl-8-phenylphenethyl)imino]azepine,
2-[(β-ethyl-8-phenylphenethyl)imino]octahydroazocine,
2-[(1,3-diphenylpentyl)imino]octahydroazonine,
2-[(1,3-diphenylpropyl)imino]piperidine,
2-(2,2-diphenylethylimino)hexahydroazepine,
2-(3,3-diphenylpropylimino)hexahydroazepine,
2-(2,3-diphenylpropylimino)azacyclotridecane,
2-[(α-methyl-β-phenylphenethyl)imino]hexahydroazepine,
2-(1,4-diphenylbutylimino)pyrrolidine,
1-methyl-2-(1,4-diphenylbutylimino)azacyclododecane,
2-[(β-phenyl-β-propylphenethyl)imino]azacyclotridecane,
2-[(β-isopropyl-β-phenylphenethyl)imino]hexahydroazepine,
2-(α-phenylphenethylimino)pyrrolidine,
2-[(α-methyl-β-phenethylpropyl)imino]octahydroazocine,
2-[(β-phenyl-β-propylphenethyl)imino]octahydroazonine,
1-butyl-2[1-(2-dibenzothienyl)ethylimino]pyrrolidine,
2-[1-(2-fluorenyl)ethylimino]hexahydroazepine,
2-[2-methyl-1-(3-phenanthryl)propylino]octahydroazocine,
2-[1-(2-dibenzofuranyl)propylimino]piperidine,
2-[1-(4-dibenzothienyl)ethylimino]hexahydroazapine,
2-[1-(2-fluorenyl)pentylimino]octahydroazonine,
2-[1-(9-phenanthryl)ethylimino]hexahydroazepine,
2-[1(2-phenanthryl)ethylimino]azacyclotridecane,
2-[1-(9,10-dihydro-2-phenanthryl)propylimino]azacyclodecane,
2-[1-(2-dibenzothienyl)ethylimino]-N-methylhexahydroazepine,
2-[1-(2-dibenzothienyl)ethylimino]octahydroazocine,
2-[(2-dibenzofuranyl)ethylimino]octahydroazonine,
2-[1-(3-phenanthryl)ethylimino]azacycloundecane,
2-[(α-cyclopropylbenzyl)imino]piperidine,
2-[(α-cyclopropyl-α-methoxybenzyl)imino]pyrrolidine,
2-[(α-cyclopropyl-p-butylbenzyl)imino]octahydroazopine,
2[(α-cyclopropyl-tert-butoxybenzyl)imino]hexahydroazepine,
2-[(α-cyclobutylbenzyl)imino]azacyclotridecane,
2-(α-cyclobutyl-2,4-diethylbenzyl)imino]octahydroazocine,
2-[(α-cyclopropylbenzyl)imino]-1-methylpyrrolidine,
2-[(α-cyclopropyl-2,4-dimethylbenzyl)imino]-1methylhexahydroazepine,
1-ethyl-2-[(α-cyclobutylbenzyl)imino]azacyclodecane,
1-propyl-2-[(o-cyclopentylbenzyl)imino]hexahydroazepine,
2-[(α-cyclobutyl-3,5-dimethoxybenzyl)imino]azacyclododecane,
2[(α-cyclopentylbenzyl)imino]octahydroazonine,
2[(α-cyclopentyl-2,4-dipropoxybenzyl)imino]azacyclotridecane,
2-[(-cyclopentyl-p-ethoxybenzyl)imino]octahydroazocine,
2-[(bis[p-ethylphenyl]methyl)imino]octahydroazocine,
2[(p-chloro-α-phenylbenzyl)imino]hexahydroazepine,
hexahydro-2 -[(α-[m-methylphenyl]-m-isopropylbenzyl)imino]octahydroazonine,
2-[(bis[p-trifluoromethylthiophenyl]methyl)imino]piperidine,
2-[(m-[trifluoromethyl]α-phenyl]benzyl)imino]hexahydroazepine,
2-[p-chloro-α-[p-chlorophenyl]benzyl)imino]azacyclodecane,
2-[(α-[p-chlorophenyl]-m-trifluoromethylbenzyl)imino]azacycloundecane,
2-[(p-tert-butyl-α-[p-chlorophenyl]benzyl)imino]azacyclododecane, 1-methyl-2-[(α-phenyl-p-trifluoromethoxybenzyl-)imino]hexahydroazepine,
2-[(p-bromo-α-phenylbenzyl)imino]azacyclotridecane,
2-[(p-phenoxy-α-phenylbenzyl)imino]azacyclotridecane,
2-[(3,4,5-trimethoxy-o-phenylbenzyl)imino]azacyclododecane,
2-[(3,4-dipropoxy-α-phenylbenzyl)imino]octahydroazopine,
2-[(bis[p-trifluoromethylthiophenyl]methyl-)imino]azacyclotridecane,
2-[(diphenylmethyl)imino]-1-methylpiperidine,
2-[(diphenylmethyl)imino]octahydroazocine,
2-[(diphenylmethyl)imino]-N-octahydroazonine,
2-[(m-methoxy-α-phenylbenzyl)imino]hexahydroazepine,
2-[(p-butoxy-α-phenylbenzyl)imino]octahydroazonine,
2-[(diphenylmethyl)imino]azacyclotridecane,
2-[(p-decyl-α-methylbenzyl)imino]pyrrolidine,
1-methyl-2-[α-methyl-p-3,3-diethylpentyl)benzylimino]pyrrolidine,
1-ethyl-2-[p-(dodecyloxy)-α-methylbenzylimino]piperidine,
2-[-methyl-p-(3,7-dimethyloctyloxy)benzylimino]-piperidine
1-propyl-2-[α-butyl-p-cyclohexylbenzylimino]hexahydroazepine,
2-[α-methyl-p-cyclododecylbenzylimino]hexahydroazepine,
2-[2,2-diphenylvinyl)-α-isopropylbenzylimino]azacyclodecane,
2-(α-methyl-p-tridecylbenzylimino)hexahydroazepine,
2-[α,2-dimethyl-4-(3-phenoxypropoxy)benzylimino]octahydroazonine,
2-[α,5-dimethyl-2-(3-phenylethoxy)benzylimino]octahydroazocine,
2-[α,3-dimethyl-4-(3-phenylpropoxy)benzylimino]hexahydroazepine,
2-(p-dodecyloxy-2-methylbenzylimino)hexahydroazepine,
1-methyl-2-[α-methyl-p-phenoxybenzylimino]azacycloundecane,
2-[α-methyl-p-(3-phenyl-1-propen-1-yl)benzylimino]azacyclotridecane,
2-[α-methyl-p-(4-phenylbutoxy)benzylimino]azacyclododecane,
2-[p-(2-phenoxyethoxy-α-methylbenzylimino]azacyclotridecane,
1-[1-(1,2,3,4-tetrahydro-6-naphthyl)ethylimino]hexahydroazepine,
2-[1-(4-indanyl)ethylimino]hexahydroazepine.
2-[1-(1,2,3,4-tetrahydro-2,2,4,4-tetramethyl-6-naphthyl)propylimino]azacyclotridecane,
1-methyl-2-[1-(4-indanyl)ethylimino]azacyclododecane,
2-[1-(1,2,3,4-tetrahydro-6-naphthyl)ethylimino]piperidine,
2-[1-(1,1-dimethyl-4-indanyl)ethylimino]azacyclotridecane, and
2-[1-(4-indanyl)ethylimino]pyrrolidine.

The compounds of this invention can be prepared as described in the prior art, i.e., U.S. Pat. No. 4,061,746.

Illustrative examples of pharmaceutically acceptable salts which may be formed of the compounds employed in the present invention are those of any suitable inorganic acids, such as hydrochloric, hydrobromic, sulfuric or phosphoric acids or any suitable organic acid, such as carboxylic acids, such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicyclic, 2-phenoxybenzoic, or sulfonic acids, such as methane sulfonic or 2-hydroxyethane sulfonic acid.

All solutions were freshly made before use and each point represents the average of three separate experiments performed in duplicate.

FIG. 2 Effect of diltiazem on Ca$^{++}$-induced contractions of K$^+$-depolarized guinea pig ileum.

Cumulative concentration response curves to Ca$^{++}$ were obtained prior to, and after, pre-incubation with different concentrations of the antagonists. Vertical bars are ±S.E.M.

- - ○- - Control 1
● Diltiazem 10$^{-7}$ M (N=4)
- - △- - Control 2
▲Diltiazem 3.16×10$^{-7}$ M (N=4)
- - □- - Control 3
- - ■- - Diltiazem 10$^{-6}$ M (N=4)

FIG. 3 Effect of Test Compound 1 on Ca$^{++}$-induced contractions of K$^+$-depolarized guinea pig ileum.

Cumulative concentration response curves to Ca$^{++}$ were obtained prior to, and after, pre-incubation with different concentrations of Test Compound 1.

- - ○- - Control 1
● Test Compound 1 10$^{-7}$ M (N=6)
- - △- - Control 2
▲ Test Compound 1 3.16×10$^{-7}$ M (N=6)
- - □- - Control 3
- - ■- - Test Compound 1 10$^{-6}$ M (N=6)

FIG. 4 Effect of Test Compound 2 on Ca$^{++}$-induced contractions of K$^+$-depolarized guinea pig ileum.

Cumulative concentration response curves to Ca$^{++}$ were obtained prior to, and after, pre-incubation with different concentrations of Test Compound 2.

- - ○- - Control 1
● Test Compound 2 10$^{-6}$ M (N=9)
- - △- - Control 2
▲ Test Compound 2 3.16$^{-6}$ M (N=7)

FIG. 5 Effect of Test Compound 3 on Ca$^{++}$-induced contractions of K$^+$-depolarized guinea pig ileum.

Cumulative concentration response curves to Ca$^{++}$ were obtained prior to, and after, pre-incubation with different concentrations of Test Compound 3.

- - ○- - Control 1
● Test Compound 3 10$^{-6}$ M (N=5)
- - △- - Control 2
▲ Test Compound 3 3.16×10$^{-6}$ M (N=7)
- - □- - Control 3
■ Test Compound 3 10$^{-5}$ M (N=5)

Figure 1B:
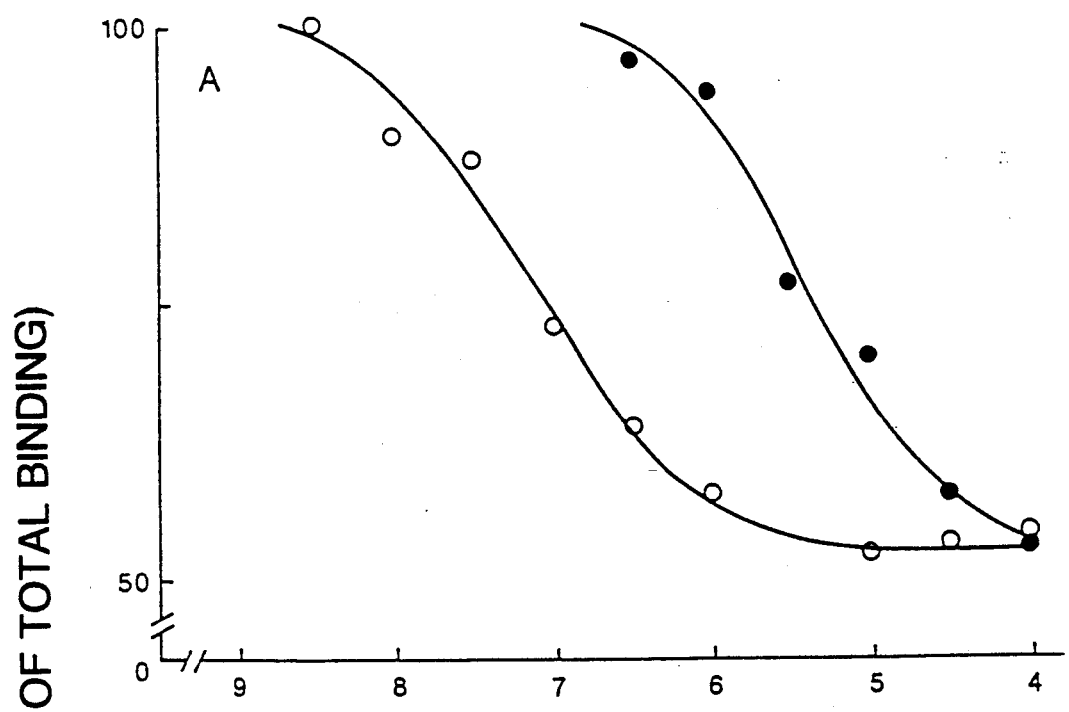
FIG. 1 Inhibition of [$^3$H]d-cis-diltiazem by d- and l-cisdiltiazem and related lactamimides The inhibition of [$^3$H]d-cis-diltiazem binding was determined by incubating [$^3$H]d-cis-diltiazem (2.5 nM) at 25° C. with six to nine concentrations of the drugs Panel A-○,d-cis-diltiazem; ●, 1-cis-diltiazem; Panel B - ○, Test Compound 3; ●, Test Compound 4,△,Test Compound 14; □, Test Compound 16; ■, Test Compound 15.
Figure 1A:
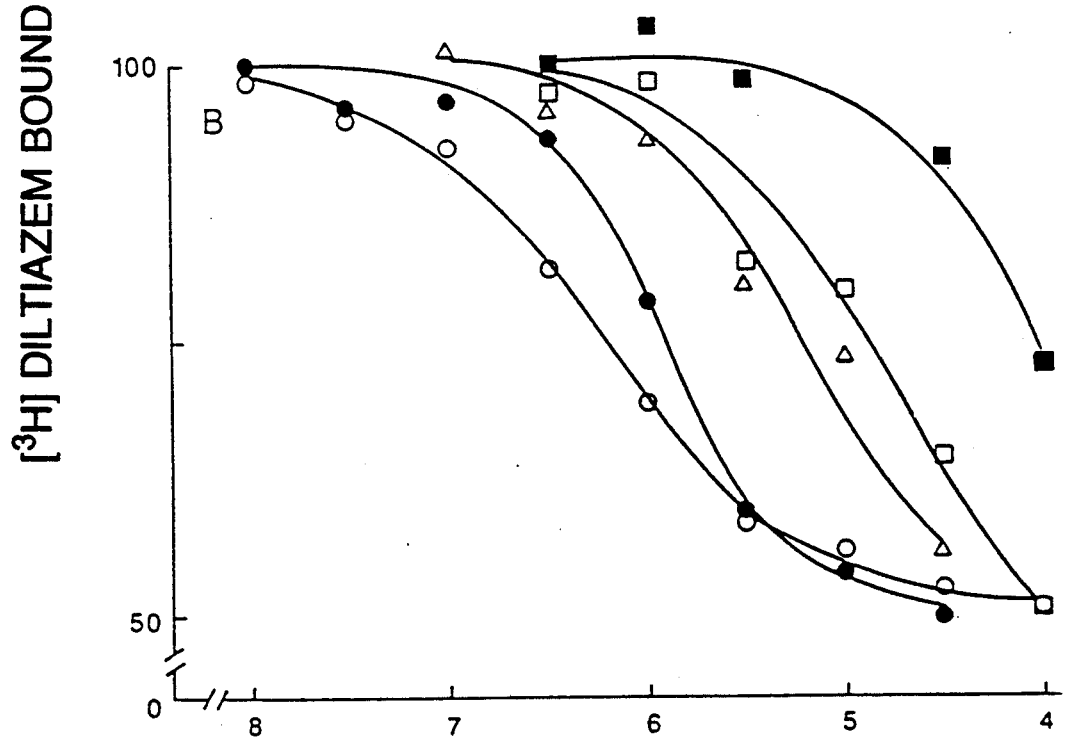
Figure 6:
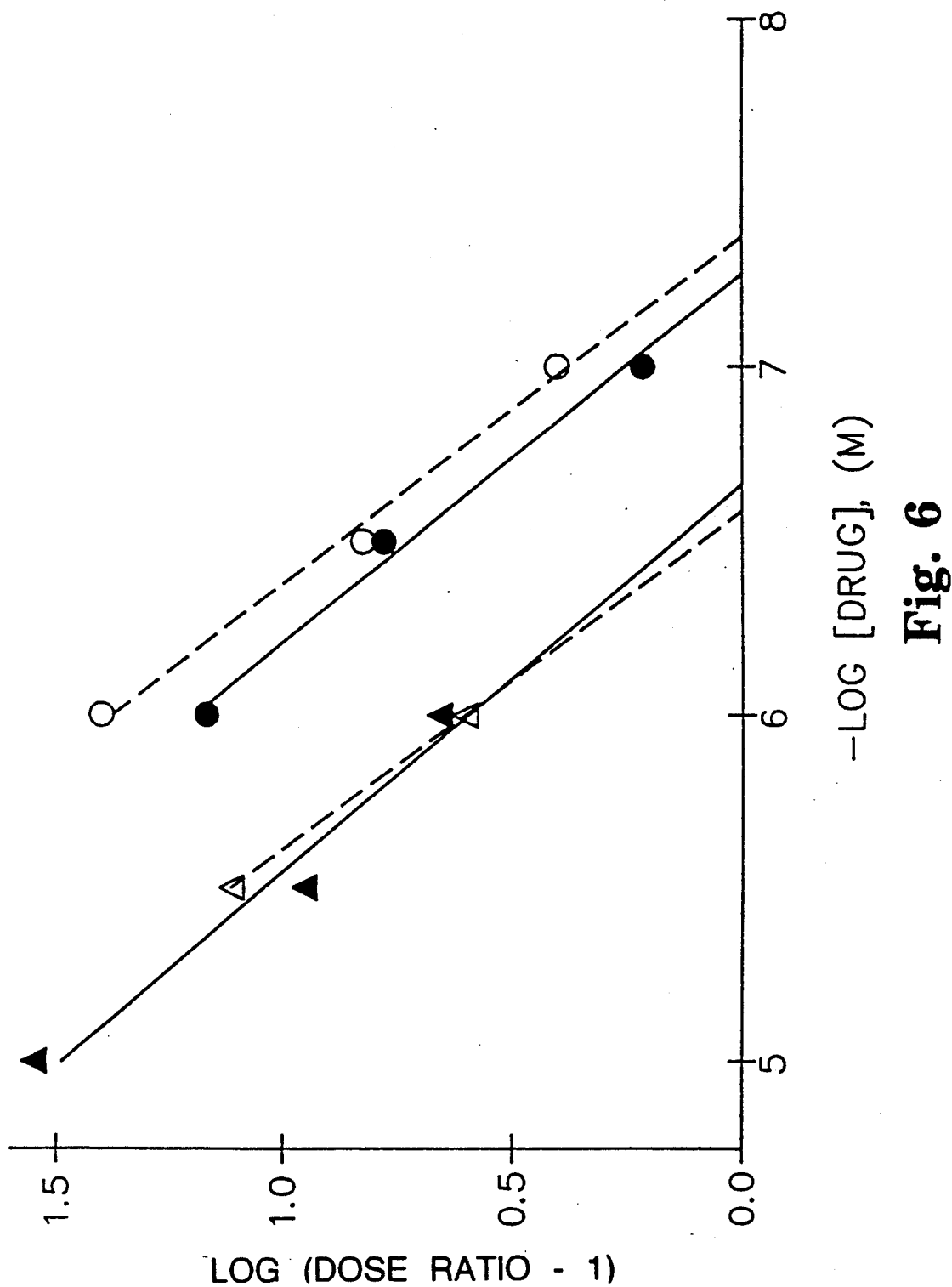

FIG. 6 Schild plot of the antagonistic effects of d-cis-diltiazem and lactamimides.

Plots of log (dose ration −1) against −log [M] gave straight lines which yielded mean pA2 values (95% confidence interval) and mean slopes (±S.D.) as follows: d-cis-diltiazem 7.38 (7.18–7.84), 1.00 (0.15); Test Compound 1 7.27 (6.95–8.12), 0.94 (0.21); Test Compound 2 6.59 (6.33–7.17), 1.02 (0.20); Test Compound 3 6.66 (6.31–7.44), 0.89 (0.16). Data were obtained from calcium dose-response curves obtained to 40 mM K+-depolarized guinea pig ileum preparations.

○ Diltiazem
● Test Compound 1
△ Test Compound 2
▲ Test Compound 3

Figure 7:
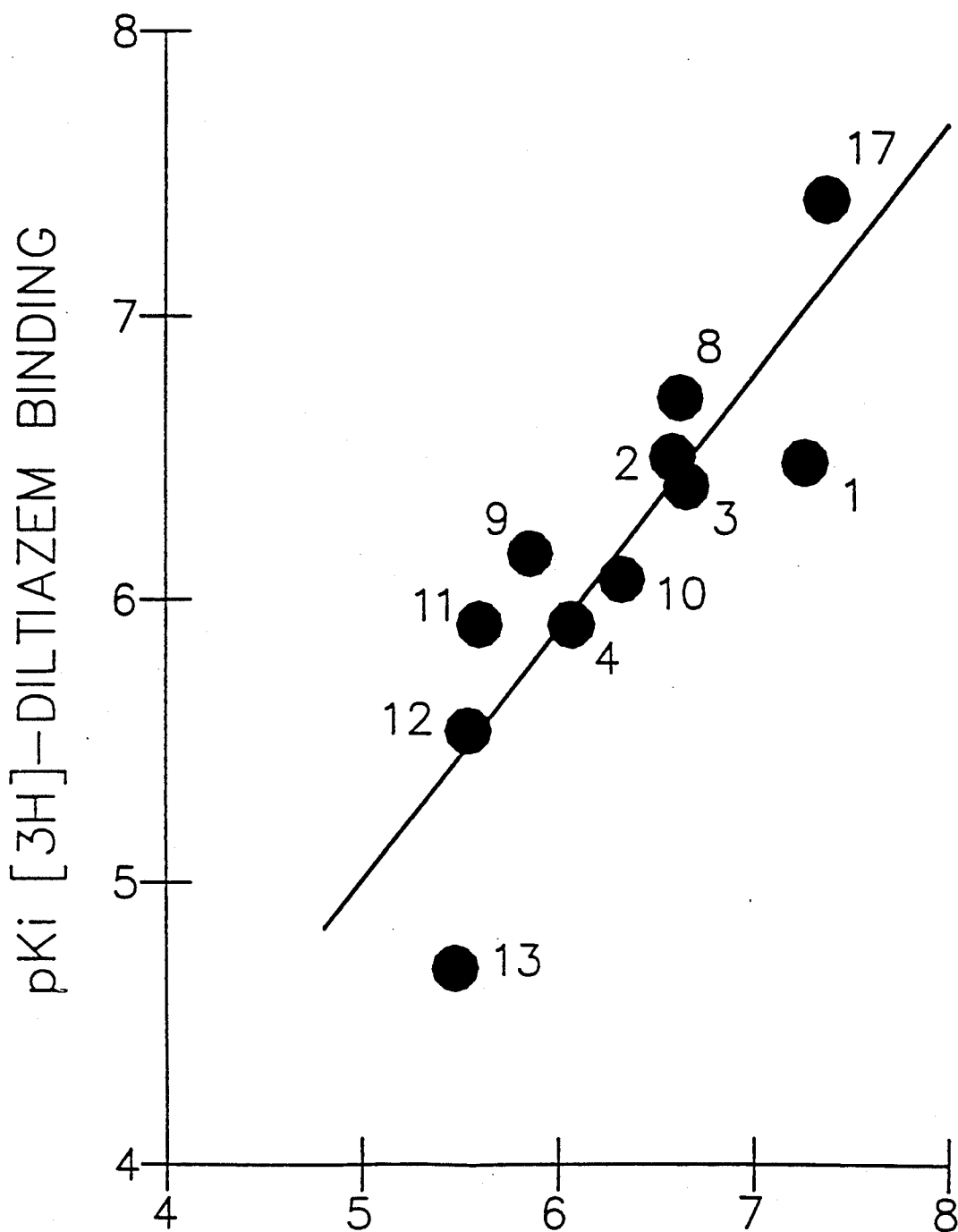

FIG. 7 Correlation between displacement of [³H]d cis-diltiazem and antagonism of Ca++-induced contractions.

The negative logarithm of the inhibitory constant (pKi, M) against [³H]d-cis-diltiazem binding in rat brain membranes was derived from the $IC_{50}$ by the Cheng and Prusoff (1973) method and is plotted against the pA2 value (M) obtained by the method of Arunlakshana and Schild (1959) using antagonism of Ca++-induced contraction of the K+-depolarized guinea pig taenia or ileum preparations. The correlation co-efficient (r=0.87, p <0.001) and the slope (0.90) were calculated by linear regression analysis.

We claim:

1. A method of effecting calcium antagonism in a patient in need thereof which comprises administering to the patient a calcium antagonism effective amount of a compound of the formula

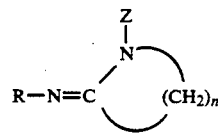

wherein
Z is hydrogen or lower alkyl of from 1 to 4 carbon atoms;
n is an integer of from 3 to 16; and
R is the group

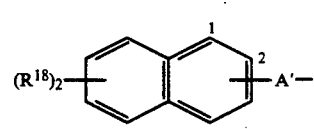

wherein
A' is a straight or branched alkylene moiety of from 1 to 6 carbon atoms or benzyl and is attached to either the 1- or 2-position of the naphthalene ring, and $R^{18}$ is hydrogen, chlorine, fluorine, bromine, trifluoromethyl, an alkyl group having from 1 to 12 carbon atoms which is straight or branched, an alkoxy group having from 1 to 3 carbon atoms or $NO_2$;
or a pharmaceutically acceptable acid addition salt thereof or an individual optical or geometric isomer.

2. The method of claim 1 wherein A' is ethyl.
3. The means of claim 1 wherein n is the integer 5.
4. The method of claim 2 wherein n is the integer 5.
5. The method of claim 1 wherein the compound is (+)-hexahydro-N-[1-(1-napthalenyl)-ethyl]2H-azepin-2-imine or a pharmaceutically acceptable salt thereof.
6. The method of claim 1 wherein the compound is (−)-hexahydro-N-[1-(1-napthalenyl)-ethyl]2H-azepin-2-imine or a pharmaceutically acceptable salt thereof.

* * * * *